United States Patent
Ueya et al.

(10) Patent No.: US 11,366,108 B2
(45) Date of Patent: Jun. 21, 2022

(54) METHOD OF PRODUCING PROBE-BOUND CARRIER, PROBE-BOUND CARRIER AND METHOD OF DETECTING OR SEPARATING TARGET SUBSTANCE

(71) Applicants: JSR CORPORATION, Minato-ku (JP); JSR LIFE SCIENCES CORPORATION, Minato-ku (JP); JSR Life Sciences, LLC, Sunnyvale, CA (US); JSR Micro N.V., Leuven (BE)

(72) Inventors: Yuuichi Ueya, Minato-ku (JP); Yasuhito Satou, Minato-ku (JP)

(73) Assignees: JSR CORPORATION, Minato-ku (JP); JSR LIFE SCIENCES CORPORATION, Minato-ku (JP); JSR Life Sciences, LLC, Sunnyvale, CA (US); JSR Micro N.V., Leuven (BE)

(*) Notice: Subject to any disclaimer, the term of this patent is extended or adjusted under 35 U.S.C. 154(b) by 33 days.

(21) Appl. No.: 15/936,807

(22) Filed: Mar. 27, 2018

(65) Prior Publication Data
US 2018/0284109 A1 Oct. 4, 2018

(30) Foreign Application Priority Data
Mar. 31, 2017 (JP) .............................. JP2017-072034

(51) Int. Cl.
*A61K 9/50* (2006.01)
*G01N 33/543* (2006.01)
*B03C 1/01* (2006.01)
*G01N 33/53* (2006.01)

(52) U.S. Cl.
CPC ......... *G01N 33/54326* (2013.01); *B03C 1/01* (2013.01); *G01N 33/5306* (2013.01); *G01N 33/54393* (2013.01); *B03C 2201/18* (2013.01)

(58) Field of Classification Search
CPC ...... A61K 9/16; A61K 9/1617; A61K 9/1682; A61K 9/50; A61K 9/501; A61K 9/5021; A61K 9/5089; A61K 9/51; G01N 33/54326; G01N 33/54333
See application file for complete search history.

(56) References Cited

U.S. PATENT DOCUMENTS

| | | | | |
|---|---|---|---|---|
| 2006/0240438 A1* | 10/2006 | Nagasaki | ......... | G01N 33/54366 435/6.19 |
| 2008/0160167 A1 | 7/2008 | Tamori et al. | | |
| 2010/0105879 A1* | 4/2010 | Katayose | ............... | C07K 17/06 530/402 |
| 2011/0311824 A1 | 12/2011 | Tamori et al. | | |
| 2012/0164214 A1* | 6/2012 | Machluf | ............ | A61K 47/6901 424/450 |
| 2013/0130280 A1* | 5/2013 | Fauconnier | ............ | G01N 33/80 435/7.25 |

FOREIGN PATENT DOCUMENTS

| | | | |
|---|---|---|---|
| CN | 101206220 A | 6/2008 | |
| CN | 106199011 A | * 12/2016 | .......... G01N 33/582 |
| CN | 106199011 A | 12/2016 | |
| JP | 57-24369 | 2/1982 | |
| JP | 61-215602 | 9/1986 | |
| JP | 61-215603 | 9/1986 | |
| JP | 61-215604 | 9/1986 | |
| JP | 3-46565 | 2/1991 | |
| JP | 2006-226691 A | 8/2006 | |
| JP | 2008-170417 | 7/2008 | |
| WO | WO 2009/028449 A1 | 3/2009 | |
| WO | WO 2012/010666 A1 | 1/2012 | |

OTHER PUBLICATIONS

Byun (Investigation of chemical modification on tosyl-activated polystyrene microsphere magnetic particle surface by infrared microscopy; Analytic Science & Technology, vol. 29, No. 5, 225-233, 2016) (Year: 2016).*

Combined Office Action and Search Report dated Feb. 15, 2019 in Chinese Patent Application No. 201810270090.4, 18 pages (with unedited computer generated English translation and English translation of categories of cited documents).

Extended European Search Report dated May 28, 2018 in European Patent Application No. 18163545.9, 7 pages.

Yan, J., et al., "A tosyl-activated magnetic bead cellulose as solid support for sensitive protein detection", Journal of Biotechnology, vol. 167 No. 3, XP028703505, Jun. 27, 2013, pp. 235-240.

Reymond, F., et al., "Fabrication and Characterization of Tosyl-Activated Magnetic and Nonmagnetic Monodisperse Microspheres for Use in Microfluic-Based Ferritin Immunoassay", Biotechnology Progress, vol. 29 No. 2, XP009505427, Apr. 2013, pp. 532-542.

European Office Action dated Dec. 2, 2019, in Patent Application No. 18 163 545.9, 6 pages.

Chinese Office Action dated Oct. 31, 2019, in Patent Application No. 201810270090.4, 19 pages (with unedited computer generated English translation).

Combined Office Action and Search Report dated Jul. 12, 2019 in Chinese Patent Application No. 201810270090.4, 18 pages (with unedited computer generated English translation and English translation of categories of cited documents).

European Office Action dated Jul. 3, 2020 in European Patent Application No. 18163545.9, 8 pages.

Office Action as received in the corresponding EP Patent Application No. 18163545.9 dated Jan. 28, 2021, 6 pages.

* cited by examiner

*Primary Examiner* — Micah Paul Young
(74) *Attorney, Agent, or Firm* — Oblon, McClelland, Maier & Neustadt, L.L.P.

(57) ABSTRACT

This invention relates to a method of producing a probe-bound carrier, a probe-bound carrier and a method of detecting or separating a target substance. The method of producing a probe-bound carrier includes: step 1 of mixing a carrier having tosyl groups and a probe; and step 2 of reducing the amount of tosyl groups on a surface of a carrier, in which a proportion of area S2 that is occupied by one tosyl group on a surface of the carrier obtained in the step 2 with respect to area S1A that is occupied by one tosyl group on a surface of the carrier used in the step 1 (S2/S1A×100%) is not less than 140%.

12 Claims, No Drawings

METHOD OF PRODUCING PROBE-BOUND CARRIER, PROBE-BOUND CARRIER AND METHOD OF DETECTING OR SEPARATING TARGET SUBSTANCE

TECHNICAL FIELD

The present invention relates to a method of producing a probe-bound carrier, a probe-bound carrier and a method of detecting or separating a target substance.

BACKGROUND ART

Carriers such as organic polymer particles and magnetic particles are used for, for example, a reaction solid phase for diagnostic agents based on antigen-antibody reactions to detect target substances (inspection targets) such as infectious disease/cancer markers and hormones. For instance, test probes (primary probes) such as antibodies or antigens are immobilized onto carriers for such diagnostic agents. An inspection target in a sample is trapped on a carrier via a primary probe and then reacts with a second test probe (secondary probe). In a case in which the secondary probe is, for example, labeled with a phosphor or an enzyme, the inspection target can be detected based on fluorescence, an enzyme reaction, or the like.

In recent years, there is a demand to achieve high sensitivity in tests for the purpose of early detection of diseases or the like. It is an important task to improve sensitivity of diagnostic agents. In order to improve sensitivity of diagnostic agents using carriers as well, there is a trend to switch the way of detection from the technology involving enzymatic color development to the technology involving fluorescence emission or chemiluminescence that can achieve improved sensitivity.

For example, magnetic particles each having tosyl groups on the surface thereof are known as carriers for the above intended use (Patent Document 1).

RELATED ART DOCUMENTS

Patent Documents

Patent Document 1: JP H3-46565 A

DISCLOSURE OF THE INVENTION

Problems to be Solved by the Invention

Conventional carriers such as magnetic particles disclosed in the above-described Patent Document are insufficient in terms of the signal/noise (S/N) ratio upon diagnosis, detection, or the like with the use of the carriers. In this regard, conventional carriers still need to be improved.

In one embodiment of the present invention, a probe-bound carrier, which is unlikely to cause non-specific adsorption of biologically relevant substances such as proteins and nucleic acids, and by which a high S/N ratio can be realized upon diagnosis, detection, or the like, and a method of producing the carrier are provided.

Means for Solving the Problems

As a result of intensive studies in order to solve the problems described above, the present inventors found that the problems can be solved based on the configuration examples described below. This has led to the completion of the present invention.

The configuration examples of the present invention are described below.

<1> A method of producing a probe-bound carrier, which comprises:
step 1 of mixing a carrier having tosyl groups and a probe; and
step 2 of reducing the amount of tosyl groups on a surface of a carrier,
wherein a proportion of area S2 that is occupied by one tosyl group on a surface of the carrier obtained in the step 2 with respect to area S1A that is occupied by one tosyl group on a surface of the carrier used in the step 1 (S2/S1A×100%) is not less than 140%.

<2> The production method according to <1>, wherein the carrier and the probe are mixed under the presence of ammonium sulfate in the step 1.

<3> The production method according to <1> or <2>, wherein a proportion of area S2 that is occupied by one tosyl group on a surface of the carrier obtained in the step 2 with respect to area S1B that is occupied by one tosyl group on a surface of the carrier obtained in the step 1 (S2/S1B×100%) is not less than 110%.

<4> The production method according to any one of <1> to <3>, wherein the step 1 comprises:
step 1a of mixing a carrier having tosyl groups with ammonium sulfate; and
step 1b of mixing in a probe after the step 1a.

<5> The production method according to any one of <1> to <4>, wherein the carrier is a magnetic particle.

<6> The production method according to <5>, wherein the magnetic particle has a core-shell structure.

<7> The production method according to <5> or <6>, wherein a volume average particle size of the magnetic particle is from 0.1 to 20 μm.

<8> The production method according to any one of <1> to <7>, wherein the step 1 is a step of mixing the carriers and the probes in a liquid containing ammonium sulfate, and an ammonium sulfate concentration in the liquid is not more than 2.0 mol/L when the carriers are brought into contact with the probes.

<9> The production method according to any one of <1> to <8>, wherein the step 1 is a step of mixing the carriers and the probes in a liquid, and pH of the liquid is from 6 to 12.

<10> The production method according to any one of <1> to <9>, wherein the area S1A that is occupied by one tosyl group on a surface of the carrier used in the step 1 is not less than 5 Å$^2$/tosyl group.

<11> The production method according to any one of <1> to <10>, wherein the probe is a protein or nucleic acid.

<12> The production method according to any one of <1> to <11>, wherein a mixing time in the step 1 is not less than 2 hours.

<13> The production method according to any one of <1> to <12>, wherein the step 2 is a step of mixing the carriers obtained in the step 1 with a blocking agent or conducting a hydrolysis reaction of the tosyl groups on a surface of the carrier, and a mixing or reaction time is not less than 2 hours.

<14> A probe-bound carrier, which is a carrier having tosyl groups, to which a probe is bound,
wherein the area that is occupied by one tosyl group on a surface of the probe-bound carrier is not less than 15 Å$^2$/tosyl group.

<15> The probe-bound carrier according to <14>, to which a blocking agent is covalently bound, <16> The probe-bound carrier according to <14> or <15>, wherein a proportion of area S2' that is occupied by one tosyl group on a surface of the probe-bound carrier with respect to area S1A' that is occupied by one tosyl group on a surface of the carrier that is not yet bound to a probe (S2'/S1A'×100%) is not less than 140%.

<17> The probe-bound carrier according to any one of <14> to <16>, which is used for an in-vitro diagnostic agent or for detection of a biologically relevant substance.

<18> A method of detecting or separating a target substance, wherein the probe-bound carrier according to any one of <14> to <16> is used.

Effect of the Invention

According to one embodiment of the present invention, it is possible to readily obtain a probe-bound carrier having high probe activity, which is unlikely to adsorb a biologically relevant substance such as a protein or nucleic acid in a non-specific manner. It is also possible to obtain high S/N ratio results using such a carrier upon diagnosis, detection, or the like, and in particular, immunoassay such as chemiluminescent immunoassay (CLIA), chemiluminescent enzyme immunoassay (CLEIA), bioluminescent enzyme immunoassay (BLEIA), or electrochemiluminescence immunoassay (ECLIA) (it is possible to realize diagnosis, detection, or the like with high sensitivity).

BEST MODE FOR CARRYING OUT THE INVENTION

Preferred embodiments according to the present invention are described in detail below. Note that the present invention is not exclusively limited to the embodiments described below. It should be understood that the present invention may encompass various modified examples within the scope that does not change the subject matter of the present invention. Any expression used herein that represents a numerical range such as "from A to B" means the same as "from not less than A to not more than B" and therefore the numerical range includes A and B.

In addition, the expression " . . . (meth)acrylate" used herein refers to a concept that encompasses both " . . . acrylate" and " . . . methacrylate." Similar expressions have the same meaning.

<Method of Producing Probe-Bound Carrier and Probe-Bound Carrier>

A method of producing a probe-bound carrier according to one embodiment of the present invention (hereinafter also referred to as "the present method") comprises: step 1 of mixing a carrier having tosyl groups and a probe; and step 2 of reducing the amount of tosyl groups on the surface of a carrier, wherein a proportion of area S2 that is occupied by one tosyl group on the surface of a carrier obtained in step 2 with respect to area S1A that is occupied by one tosyl group on the surface of the carrier used in step 1 (S2/S1A× 100%) is not less than 140%.

A probe-bound carrier according to one embodiment of the present invention is a carrier having tosyl groups, to which a probe is bound, and in which area S2' that is occupied by one tosyl group on the surface of the probe-bound carrier is not less than 15 Å²/tosyl group.

The method of producing the probe-bound carrier is not particularly limited. The method is preferably the present method while it may be a conventional method.

<Step 1>

Step 1 described above is not particularly limited as long as a carrier having tosyl groups is mixed with a probe. However, step 1 is preferably a step of mixing the carrier and the probe in a liquid from the viewpoint that, for example, the carrier is readily brought into contact with the probe, thereby making it possible to conveniently obtain a desirable probe-bound carrier. In such a case, a liquid may be added to and mixed with a mixture of the carrier and the probe. Alternatively, the carrier may be added to and mixed with a probe dispersion liquid or a probe-containing sample. However, it is preferable to add a probe to a dispersion liquid of the carrier.

The way of mixing is not particularly limited. In a case in which the carrier is mixed with a probe in a liquid, the liquid may be simply allowed to standstill or may be stirred, for example.

Time required for mixing in step 1 may differ depending on conditions such as types and weights of a carrier and a probe to be used. However, the mixing time is preferably not less than 2 hours, more preferably not less than 6 hours, and particularly preferably not less than 8 hours from the viewpoint that, for example, a probe-bound carrier, to which a probe is sufficiently bound, can be obtained. The mixing time is also preferably not more than 48 hours, more preferably not more than 36 hours, and particularly preferably not more than 24 hours from the viewpoint that, for example, a probe-bound carrier can be efficiently produced.

Step 1 may be conducted at room temperature or during heating.

The heating temperature may be appropriately selected depending on conditions such as types of a carrier and a probe to be used. However, the heating temperature is preferably from 4° C. to 50° C., more preferably from 20° C. to 45° C., and particularly preferably from 35° C. to 40° C. from the viewpoint that, for example, a probe-bound carrier can be efficiently produced while probe activity is maintained.

In a case in which step 1 is a step of mixing carriers and probes in a liquid, pH of the liquid is preferably from 6 to 12, more preferably from 7 to 11, and particularly preferably from 8 to 10 from the viewpoint that, for example, the amount of probes bound to carriers is improved.

Step 1 is usually conducted in the air. However, it may be conducted in a specific gas atmosphere such as an inert gas atmosphere or in a specific container or system such as a grow box depending on a carrier and a probe to be used, for example.

Step 1 is preferably a step of mixing the carrier and the probe under the presence of ammonium sulfate.

The presence of ammonium sulfate in a system for mixing the carrier and the probe allows the amount of probes bound to carriers to increase. In a particular case in which a highly hydrophilic probe is used, although the amount of probes bound to carriers tends to decrease, a probe-bound carrier, which achieves a large amount of probes bound to carriers, can be readily obtained by performing salting-out to make a protein or the like hydrophobic even with the use of such probes.

Step 1 is preferably a step that includes step 1a of mixing the carrier with ammonium sulfate and step 1b of mixing a probe with the liquid obtained in step 1a. Such a step allows preventing probes from being exposed to locally highly concentrated ammonium sulfate. This makes it difficult for probes to be precipitated or aggregated, thereby allowing the probes to be bound to carriers more evenly. Accordingly, low noise and high signals can be achieved upon diagnosis, detection, or the like with the use of the obtained carrier.

For the same reason, step 1 is also preferably a step of mixing a carrier with a probe in a liquid containing ammonium sulfate. In such a case, the ammonium sulfate concentration in a liquid in which the carrier is brought into contact with the probe may be adjusted depending on hydrophilicity of the probe. However, the concentration is, but is not particularly limited to, preferably from not more than 2.0 mol/L, more preferably from 0.1 to 2.0 mol/L, and particularly preferably from 0.2 to 1.0 mol/L.

In a case in which the ammonium sulfate concentration is less than the lower limit, it might be difficult to bind a sufficient amount of probes to carriers. This may cause signal reduction upon diagnosis, detection, or the like with the use of the obtained carrier. In a case in which the ammonium sulfate concentration exceeds the upper limit, probes tend to be precipitated or aggregated, which may cause signal reduction upon diagnosis, detection, or the like with the use of the obtained carrier.

In a usual case in which hydroxyl groups protected with tosyl groups are bound to amino groups or the like of probes, if probes have low hydrophilicity and tend to interact with carrier surfaces, ammonium sulfate is used at a low concentration or is not necessary. However, it was found that in a case in which highly hydrophilic probes are used, carrier-binding efficiency significantly declines. In a case in which highly hydrophilic probes are used, it is necessary to reduce hydrophilicity of probes so as to facilitate probes to interact with carrier surfaces in order to improve carrier-binding efficiency of probes. However, when the ammonium sulfate concentration falls within the above range, probes are unlikely to be precipitated until the completion of binding of a sufficient amount of probes, which is preferable. In addition, when the ammonium sulfate concentration falls within the above range, it is possible to prevent probes from being denatured or aggregated. It is therefore possible to readily obtain a probe-bound carrier, to which a probe is sufficiently bound, and in which probe characteristics are not impaired (probe activity is high), thereby making it possible to obtain high S/N ratio results using the carrier upon diagnosis, detection, or the like, and in particular, immunoassay such as CLIA or CLEIA (to realize diagnosis, detection, or the like with high sensitivity).

In a case in which step 1 is conducted in a liquid, the liquid is not particularly limited, and it may be selected depending on a carrier and a probe to be used. However, an aqueous medium is usually used from the viewpoint that, for example, it can be preferably used for biochemical purposes and the like, it is less likely to negatively affect the environment, and it is highly safe for a worker who handles it. More specifically, a variety of buffer solutions, water, and a mixed solvent of water and an organic solvent such as alcohol which is mixed with water at an arbitrary ratio, and the like are used. Of these, buffer solutions are preferable. A buffer solution having buffering capacity at pH of 6 to 12 is preferable, a buffer solution having buffering capacity at pH of 7 to 11 is more preferable, and a buffer solution having buffering capacity at pH of 8 to 10 is particularly preferable. In addition, it is preferable for such buffer solution not to contain components that react with tosyl groups. One example is a buffer solution of sodium borate.

The aqueous medium is not particularly limited as long as it contains water, and it may contain one or more types of non-aqueous media other than water.

Further, the liquid may contain conventionally known additives, in addition to the carrier, probe, ammonium sulfate, and aqueous medium. Examples of such additives include surfactants, dispersants, pH adjusters, salts, and stabilizers such as polymers.

<Carrier Having Tosyl Groups>

The carrier is not particularly limited as long as it has tosyl groups on its surface. Usually, a probe can be chemically bound to the surface of the carrier having tosyl groups only by mixing or bringing the carrier with or into contact with the probe. Therefore, a carrier having tosyl groups is preferably used. In addition, even without the use of a condensation agent or the like, as the carrier has tosyl groups, a probe can be bound to the carrier. Accordingly, by using the carrier, it is possible to readily obtain a probe-bound carrier for conveniently carrying out diagnosis, detection, or the like.

Two or more types of carriers may be used in step 1. However, one type of carrier is usually used.

Note that the term "tosyl group" used in the present invention refers to a p-toluenesulfonyl group.

The form of the carrier is not particularly limited, and it may be any of a particle form, a plate form, a filter form, a sheet form, and the like. However, a particle form is preferable. Examples of a particle-form carrier include a particle formed with an organic polymer, a particle formed with an inorganic material, and a particle comprising an organic polymer and an inorganic material. Of these, an organic polymer particle comprising an organic polymer is preferable from the viewpoint that, for example, it is light, and a desirable particle can be readily formed.

The organic polymer particle may be a cross-linked polymer or a non-cross-linked polymer. However, it may be preferably a particle having a cross-linked polymer at least on its surface. In the case of conducting the present method in a liquid, the cross-linked structure formed with a cross-linked polymer makes it possible to inhibit dissolution of particles in the liquid or swelling of particle surfaces due to the liquid. In the case of conducting the present method in a liquid when an organic polymer particle does not have a cross-linked polymer at least on its surface, the particle surface may be dissolved in the liquid, which might result in reduction of sensitivity due to detachment of a probe bound to the particle, or the liquid may cause swelling of the particle surface, which might promote non-specific adsorption of a biologically relevant substance.

Note that the expression "having . . . at least on its particle surface" used in the present invention refers to a component that constitutes the particle surface. This, however, does not necessarily mean a requirement that an organic polymer particle has a core-shell structure. Therefore, the organic polymer particle as a whole may be formed with a cross-linked polymer.

The carrier is preferably a magnetic particle having a magnetic body. It becomes easy to, for example, remove components bound to the carrier and the other components by using a magnetic particle as the carrier, thereby making it possible to remarkably simplify the operation of diagnosis, detection, separation, or the like.

Specific examples of the magnetic particle include the following particles (i) to (iv). Of these, a particle (ii) or (iii) having a core-shell structure is preferable and a particle (iii) is more preferable from the viewpoint that, for example, the particle size or magnetic body content can be readily adjusted.

(i) Particle having a continuous phase containing an organic polymer or an inorganic material such as silica, in which magnetic body particles are dispersed (ii) Particle having a core formed with a magnetic body particle or a secondary aggregate of magnetic body particles and a shell formed with an organic polymer or an inorganic material such as silica (iii) Particle having a core formed with a base particle that has a nuclear particle comprising an organic polymer or an inorganic material such as silica and a magnetic body layer (secondary aggregate layer) comprising magnetic body particles formed on the surface of the nuclear particle and having a shell that is a layer comprising an organic polymer (iv) Particle that is a porous particle consisting of an organic polymer or an inorganic material having pores, in which magnetic body particles are dispersed, which the particle may be provided with a layer comprising an organic polymer as a shell in the outermost layer of the particle The organic polymer is not particularly limited, and therefore, it may be a natural polymer such as agarose, dextran, or cellulose or a synthetic polymer. Examples of the organic polymer include polymers obtained from one or more types of polymers selected from monofunctional monomers and cross-linking monomers.

Examples of monofunctional monomers include: monofunctional aromatic vinyl monomers such as styrene, α-methylstyrene, and halogenated styrene; monofunctional (meth)acrylate monomers such as methyl(meth)acrylate, ethyl(meth)acrylate, stearyl(meth)acrylate, cyclohexyl (meth)acrylate, isobornyl(meth)acrylate, 2-amino ethyl (meth)acrylate, and 1,4-cyclohexanedimethanol mono (meth)acrylate; glycidyl group-containing monomers such as glycidyl(meth)acrylate, allylglycidylether, 3,4-epoxycyclohexyl(meth)acrylate, and methylglycidyl(meth)acrylate; hydroxyl group-containing monomers such as 2-hydroxyethyl(meth)acrylate, 2-hydroxyethyl(meth)acrylamide, 2-hydroxypropyl(meth)acrylate, 2-hydroxypropyl(meth) acrylamide, 2-hydroxybuthyl(meth)acrylate, 2-hydroxybuthyl(meth)acrylamide, glycerol mono(meth)acrylate, and glycerol mono(meth)acrylamide.

Examples of cross-linked monomers include polyfunctional aromatic vinyl monomers such as divinyl benzene; polyfunctional (meth)acrylate monomers such as ethylene glycol di(meth)acrylate, trimethylolpropane tri(meth)acrylate, dipentaerythritol hexa(meth)acrylate, and allyl(meth) acrylate; and conjugated diolefins such as butadiene and isoprene.

It is preferable to use one or more types of glycidyl group-containing monomers and hydroxyl group-containing monomers for the organic polymer from the viewpoint that, for example, tosyl groups can be readily introduced into the surface of a carrier.

The particle (iii) is described below.

The nuclear particle is basically a non-magnetic substance. Either an organic substance or an inorganic substance can be used therefor and appropriately selected depending on the intended use of a probe-bound carrier or the like. However, a particle consisting of an organic polymer is preferable in view of workability upon conjugation, lightweight properties, and the like.

An organic polymer that constitutes the nuclear particle is preferably a vinyl polymer and more preferably cross-linked polystyrene, cross-linked acrylate, or cross-linked polymethyl methacrylate. A functional group such as a carboxyl group may be introduced into these polymers.

Such a nuclear particle can be produced in accordance with conventional methods such as the methods described in JP S57-24369 B, JP S61-215602 A, JP S61-215603 A, and JP S61-215604 A.

The volume average particle size (hereinafter also simply referred to as "particle size") of the nuclear particle can be measured by the method described in the Examples. The particle size is preferably from 0.1 to 10 μm, more preferably from 0.2 to 5 μm, and particularly preferably from 0.3 to 2 μm from the viewpoint that, for example, excellent magnetic separation property is achieved, gravitational sedimentation is unlikely to occur, and a uniform reaction field can be generated.

Examples of the magnetic body include triiron tetraoxide ($Fe_3O_4$), diiron trioxide ($\gamma$-$Fe_2O_3$), various ferrites, metals such as iron, manganese, nickel, cobalt and chromium, and alloys of cobalt, nickel and manganese.

Of these, iron oxide superparamagnetic fine particles having particle sizes of not more than 50 nm and preferably from 5 to 30 nm are preferable. Superparamagnetic fine particles containing ferrite represented by $AFe_2O_4$(A denotes Mn, Co, Ni, Mg, Cu, Zn, $Li_{0.5}Fe_{0.5}$, or the like), magnetite ($Fe_3O_4$), or $\gamma$-$Fe_2O_3$ are more preferable. Superparamagnetic fine particles consisting of $\gamma$-$Fe_2O_3$ and/or $Fe_3O_4$ are particularly preferable because of strong saturated magnetization and few residual magnetizations.

Note that the particle size of the magnetic body is an average value of particle sizes of 100 particles randomly selected in an electron microscopic image.

The magnetic body particle is preferably a surface-hydrophobized particle.

A method of hydrophobizing the surface of a magnetic body particle is not particularly limited. However, examples of the method include a method in which a hydrophobic substance that has a portion having high affinity for a magnetic body particle and a hydrophobic portion in its molecule is brought into contact with a magnetic body particle, thereby binding the hydrophobic substance and the magnetic body particle. Specific examples of the method include a method in which a particle is obtained from a commercially available oily magnetic fluid and the particle is dried.

The amount of the magnetic body particle used may be changed, if appropriate, depending on the particle size of a base particle, a magnetic body particle or the like, and therefore, it is not particularly limited. However, the magnetic body particle is used preferably in an amount that allows a plurality of magnetic body particles to cover the entire nuclear particle surface and more preferably in an amount that allows a mass ratio of the nuclear particle and the magnetic body particle to become 10:1 to 1:3.

A method of producing a base particle in which a layer of the magnetic body layer is formed on the surface of a nuclear particle is not particularly limited. However, examples thereof include a method in which a nuclear particle such as an organic polymer particle that is a non-magnetic body and a magnetic body particle are dry-blended and physical force is externally applied, thereby conjugating both particles.

Examples of a method of applying physical force include a method using a mortar, an automatic mortar, or a ball mill, a method of powder compression by blade pressurization, a method utilizing mechanochemical effects such as a mechanofusion method, and a method utilizing an impact given by a high-speed airstream using a jet mill, a hybridizer, or the like. In order to efficiently achieve strong conjugation, it is preferable that physical adsorption capacity is strong. This can be achieved by, for example, stirring in a container equipped with a stirring blade at a circumferential velocity of the stirring blade of preferably not less than 15 m/second, more preferably not less than 30 m/second, and further preferably from 40 to 150 m/second. In a case in which the circumferential velocity of the stirring blade is below 15 m/second, it might be unable to allow a magnetic body particle to be sufficiently adsorbed to the surface of a nuclear particle. In addition, although the upper limit of the circumferential velocity of the stirring blade is not particularly limited, it may be determined depending on a system to be used, energy efficiency, and other conditions.

The shell can be formed by, for example, carrying out polymerization in a liquid to which main materials (e.g., one or more types of the above-described monofunctional monomers and cross-linking monomers) and, if necessary, auxiliary materials (e.g., a polymerization initiator, an emulsifier, a dispersant, a surfactant, an electrolyte, a cross-linking agent, and a molecular weight adjuster) have been added under the presence of base particles prepared in the manner described above.

The organic polymer particle or magnetic particle has tosyl groups on its surface. A method of producing a particle having tosyl groups on its surface may be, for example, a method of preparing a particle using a monomer having tosyl groups or a method of generating tosyl groups via a reaction for forming a shell or the like. However, a method, in which a particle having hydroxyl groups on its surface is prepared and then the hydroxyl groups are allowed to react with a tosyl group-containing compound such as p-toluenesulfonyl chloride under the presence of amine or the like, thereby introducing tosyl groups, is preferable from the viewpoint that, for example, a desirable carrier can be readily obtained.

The method of producing a particle having hydroxyl groups on its surface is not particularly limited and may be carried out in accordance with a conventionally known method. However, the method is preferably, for example, a method in which the hydroxyl group-containing monomer is used as an organic polymer for forming the shell or a method in which a glycidyl group-containing monomer is used as an organic polymer for forming the shell and the glycidyl group is made ring-opened with an acid or the like.

The hydroxyl group is preferably a 2,3-dihydroxypropyl group ($-CH_2CH(OH)CH_2(OH)$) from the viewpoint that, for example, tosyl groups can be efficiently and readily introduced into the surface of a carrier.

A carrier, into which tosyl groups are not yet introduced, is preferably highly hydrophilic. Such a carrier has a contact angle with water (25° C.) is preferably not more than 400, more preferably not more than 300, and particularly preferably from 100 to 250.

When the contact angle falls within the above range, a probe-bound carrier, by which a high S/N ratio can be achieved upon diagnosis, detection, or the like, can be readily obtained. When the contact angle exceeds the upper limit of the range, non-specific adsorption of a biologically relevant substance to a probe-bound carrier may be promoted.

In the present invention, in a case in which a carrier is in the particle form, the contact angle is measured using a dry coating film formed with the carrier.

The dry coating film is a coating film obtained by applying 0.2 mL of a water dispersion liquid containing 50 mg of carrier particles to a smooth base material such as a glass slide using an applicator and drying the water dispersion liquid at a humidity of 40% and an air temperature of 25° C. for 24 hours.

The contact angle between the dry coating film and water is determined by dropwise adding about 1 µL of a droplet of water (25° C.) to the dry coating film, immediately taking an image of the coating film from the horizontal direction, and obtaining an angle between the horizontal line of the coating film and the contour of the droplet, which is assumed as a part of a circumference of a circle.

A carrier having a contact angle that falls within the above range, into which tosyl groups are not yet introduced, can be prepared by adjusting conditions such as the amount and type of a monomer used for forming a particle (surface).

Tosyl groups can be introduced by allowing at least one hydroxyl group on the surface of the particle to react with a tosyl group-containing compound.

Therefore, a particle obtained by introducing tosyl groups into a particle having 2,3-dihydroxypropyl groups may be a particle having any of 2-hydroxy-3-(4'-methylphenyl) sulfonyloxypropyl groups, 3-hydroxy-2-(4'-methylphenyl) sulfonyloxypropyl groups, and 2,3-di(4'-methylphenyl) sulfonyloxypropyl groups.

Remaining untosylated hydroxyl groups contribute to making a carrier hydrophilic, and thus, they tend to contribute to lowering noise upon diagnosis, detection or the like.

Particle Size

In a case in which the carrier is a particle and preferably a magnetic particle, the particle size of the carrier is preferably from 0.1 to 20 µm, more preferably from 0.2 to 15 µm, and particularly preferably from 0.3 to 10 µm.

When the particle size falls within the above range, a carrier having a large amount of probes bound per unit volume can be readily obtained. By using such a carrier, sensitivity upon diagnosis, detection, or the like can be improved. In a case in which the particle size is below the lower limit of the above range, separation by centrifugation or the like tends to become time-consuming. In addition, separation of particles from a washing solvent such as water tends to become insufficient, which may result in insufficient removal of undesirable molecules (e.g., a biologically relevant substance such as a protein or nucleic acid). This makes it impossible to carry out sufficient purification in some cases. Meanwhile, when the particle size exceeds the upper limit of the above range, the specific surface area tends to decrease and the amount of carrier-bound probes tends to decrease, which may result in low sensitivity.

The particle size is determined by the pore electrical resistance method (electrical sensing zone method). Details are described later.

Area Occupied by One Tosyl Group on the Surface of Carrier

The area occupied by one tosyl group on the surface of a carrier (either area S1A that is occupied by one tosyl group on the surface of a carrier used in step 1 or area S1A' that is occupied by one tosyl group on the surface of a carrier to which a probe is not yet bound) is preferably not less than 5 $Å^2$/tosyl group, more preferably not less than 10 $Å^2$/tosyl group, and particularly preferably not less than 20 $Å^2$/tosyl group, and it is preferably not more than 80 $Å^2$/tosyl group, more preferably not more than 60 $Å^2$/tosyl group, and particularly preferably not more than 40 $Å^2$/tosyl group.

In a case in which either the S1A or S1A' falls within the above range, a probe-bound carrier, by which a high S/N ratio can be achieved upon diagnosis, detection, or the like, can be readily obtained.

In a case in which the areas S1A and S1A' are below the lower limit of the above range, as the density of tosyl groups on the surface of a carrier is high, a probe tends to be bound at multi sites on the surface of a carrier, which might cause signal reduction due to denaturation of probes. In addition, an excess of tosyl groups tends to remain on a probe-bound carrier, which tends to make the surface of the carrier more hydrophobic. Accordingly, it might cause an increase in noise upon diagnosis, detection, or the like with the use of the carrier. Meanwhile, in a case in which the areas S1A and S1A' exceed the upper limit of the above range, it is likely impossible to bind a sufficient amount of probes to carriers. This might cause signal reduction upon diagnosis, detection, or the like with the use of the carrier.

As a result of intensive studies, the present inventors found that in a case in which the carrier is a particle containing an organic polymer, upon measurement of the amount of tosyl groups in an organic medium, not only tosyl groups present on the surface of the carrier but also tosyl groups present inside of the carrier are measured together due to swelling of the carrier, and therefore, such a measurement method is not appropriate as a method of evaluating properties of the surface of the carrier. Accordingly, the present inventors succeeded in quantitatively determining the amount of tosyl groups on the surface of the carrier exclusively by determining the amount of tosyl groups on the surface of the carrier in an aqueous medium. Details are described below. As a result, it has become possible to evaluate the amount of tosyl groups involved in binding of probes and the amount of tosyl groups that may cause non-specific adsorption.

The area occupied by one tosyl group is a value obtained by measurement in an aqueous medium according to the present invention. Details are described below.

Contact Angle

An angle formed between the surface of a carrier having tosyl groups and water (25° C.) is preferably not less than 50°. In a case in which the carrier is in the particle form, a contact angle formed between a dry coating film consisting of the carrier and water (25° C.) is preferably not less than 70°, more preferably not less than 90°, and particularly preferably not from 105° to 120°.

When the contact angle falls within the above range, a probe-bound carrier, by which a high S/N ratio can be achieved upon diagnosis, detection, or the like, can be readily obtained. When the contact angle is below the lower limit of the above range, sensitivity upon diagnosis, detection, or the like with the use of the obtained probe-bound carrier might decrease.

In addition, by using a carrier for which a contact angle before introduction of tosyl groups falls within the above range and a contact angle after introduction of tosyl groups also falls within the above range, it is possible to inhibit non-specific adsorption of a biologically relevant substance to the probe-bound carrier, thereby achieving high sensitivity upon diagnosis, detection, or the like with the use of the probe-bound carrier.

A carrier having tosyl groups for which the contact angle falls within the above range can be adjusted depending on the degree of introduction of tosyl groups or the like.

<Probe>

The above-described probe is not particularly limited, and it may be a substance used for diagnosis, detection, or the like. However, the probe is preferably a specific binding substance. Specifically, it is preferably a protein or nucleic acid, more preferably an antigen, antibody, or avidin, and particularly preferably an antigen or antibody.

Two or more types of probes may be used in step 1. However, one type of probe is usually used.

The antigen or antibody preferably reacts with a component usually contained in a test object. Examples thereof include: antigens or antibodies for coagulation/fibrinolysis-related tests such as an anti-antiplasmin antibody for antiplasmin test, an anti-D dimer antibody for D dimer test, an anti-FDP antibody for FDP test, an anti-tPA antibody for tPA test, an anti-TAT complex antibody for TAT test, and an anti-FPA antibody for FPA test; antigens or antibodies for tumor-related tests such as an anti-BFP antibody for BFP test, an anti-CEA antibody for CEA test, an anti-AFP antibody for AFP test, an anti-ferritin antibody for ferritin test, and an anti-CA19-9 antibody for CA19-9 test; antigens or antibodies for serum protein-related tests such as an anti-apolipoprotein antibody for apolipoprotein test, an anti-$\beta$2-microglobulin antibody for $\beta$2-microglobulin test, an anti-$\alpha$1-microglobulin antibody for $\alpha$1-microglobulin test, an anti-immunoglobulin antibody for immunoglobulin test, and an anti-CRP antibody for CRP test; antigens or antibodies for endocrine function tests such as an anti-HCG antibody for HCG test; antigens or antibodies for infectious disease-related tests such as an anti-HBs antibody for HBs antigen test, an HBs antigen for HBs antibody test, an HCV antigen for HCV antibody test, an HIV-1 antigen for HIV-1 antibody, an HIV-2 antigen for HIV-2 antibody test, an HTLV-1 antigen for HTLV-1 test, a mycoplasma antigen for mycoplasma infection test, a toxoplasma antigen for toxoplasma test, and a streptolysin O antigen for ASO test; antigens or antibodies for autoimmunity-related tests such as a DNA antigen for anti-DNA antibody test and heat-denatured human IgG for RF test; and antigens or antibodies for drug analysis such as an anti-digoxin antibody for digoxin test and an anti-lidocaine antibody for lidocaine test.

The antibody to be used may be either a polyclonal antibody or a monoclonal antibody.

Examples of the above-described highly hydrophilic probe include a probe that is not precipitated upon salting-out even in an aqueous solution or buffer solution containing the probe at 1% by mass and ammonium sulfate at 33% by mass.

It is preferable to use probes in step 1 in an amount at which the proportion of area S1B that is occupied by one tosyl group on the surface of a carrier obtained in step 1 with respect to area S1A that is occupied by one tosyl group on the surface of a carrier to be used (before being bound to a probe) in step 1 (S1B/S1A×100%) falls within the range described below from the viewpoint that, for example, high sensitivity can be achieved upon diagnosis, detection, or the like with the use of the obtained probe-bound carrier.

In one aspect in which a magnetic particle is used as a carrier, the amount of probes used in step 1 is preferably not less than 0.5 parts by mass and more preferably not less than 1 part by mass with respect to 100 parts by mass of magnetic particles from the viewpoint that, for example, high sensitivity can be achieved upon diagnosis, detection, or the like with the use of the obtained probe-bound carrier. In addition, the upper limit thereof is preferably not more than 200 parts by mass and more preferably not more than 100 parts by mass.

Area S1B Occupied by One Tosyl Group on the Surface of Carrier Obtained in Step 1

The area S1B that is occupied by one tosyl group on the surface of a carrier obtained in step 1 is preferably not less than 10 Å$^2$/tosyl group, more preferably not less than 25 Å$^2$/tosyl group, and particularly preferably not less than 40 Å$^2$/tosyl group.

When the area S1B falls within the above range, a probe-bound carrier, by which a high S/N ratio can be achieved upon diagnosis, detection, or the like, can be readily obtained.

The proportion of area S1B that is occupied by one tosyl group on the surface of a carrier obtained in step 1 with respect to area S1A that is occupied by one tosyl group on the surface of a carrier used in step 1 (S1B/S1A×100%) is preferably not less than 110%, more preferably not less than 120%, and particularly preferably not less than 130%.

When the proportion of the area falls within the above range, a probe-bound carrier, by which a high S/N ratio can be achieved upon diagnosis, detection, or the like, can be readily obtained.

<Step 2>

Step 2 described above is not particularly limited as long as it is a step of reducing the amount of tosyl groups on the surface of a carrier, however, it is preferably a step of allowing tosyl groups on the surface of a carrier to be released. Step 2 is usually carried out after step 1.

Tosyl groups remaining after step 1 are highly hydrophobic, and therefore, they tend to cause non-specific adsorption of a biologically relevant substance. The use of a carrier having remaining tosyl groups upon diagnosis, detection, or the like tends to cause an increase in noise. It is therefore preferable to reduce the amount of tosyl groups on the surface of a carrier obtained in step 1 and it is particularly preferable to allow tosyl groups to be chemically released.

Specific examples of a method used in step 2 include a method in which tosyl groups are hydrolyzed with acid or alkali so as to be released and a method in which tosyl groups are allowed to react with a blocking agent so as to be released. Step 2 may be carried out by either one of or two or more of such methods.

It is preferable to employ a method in which a blocking agent is allowed to react with tosyl groups in step 2 from the viewpoint that, for example, non-specific adsorption capacity of the obtained probe-bound carrier can be inhibited to a greater extent.

When the blocking agent is allowed to react with tosyl groups, it is not particularly limited as long as a carrier is mixed with a blocking agent. However, it is preferable to employ a method of mixing a carrier and a blocking agent in a liquid from the viewpoint that, for example, the carrier and the blocking agent are readily brought into contact with each other, thereby conveniently obtaining a desirable probe-bound carrier. A liquid used in this method is, for example, a liquid similar to the liquid described for step 1 above. In a case in which step 1 is conducted in a liquid, the liquid used in step 1 may be directly used in step 2.

The way of mixing is not particularly limited. In a case in which the carrier is mixed with the blocking agent in a liquid, the liquid may be simply allowed to stand still or may be stirred, for example.

Time required for mixing (time required for a reaction of a carrier and a blocking agent) or time required for a hydrolysis reaction would differ depending on conditions such as types and amounts of a carrier and a blocking agent to be used. However, such time is preferably not less than 2 hours, more preferably not less than 6 hours, and particularly preferably not less than 8 hours from the viewpoint that, for example, blocking is conducted to a sufficient extent, thereby making it possible to readily obtain a probe-bound carrier for which the area S2 falls within the range described below. The time is also preferably not more than 48 hours, more preferably not more than 36 hours, and particularly preferably not more than 24 hours from the viewpoint that, for example, a probe-bound carrier can be efficiently produced.

Step 2 may be conducted at room temperature or during heating.

The heating temperature may be appropriately selected depending on conditions such as types of a carrier and a blocking agent to be used. However, the heating temperature is preferably from 4° C. to 50° C., more preferably from 20° C. to 45° C., and particularly preferably from 35° C. to 40° C. from the viewpoint that, for example, a specific probe-bound carrier can be efficiently produced.

Step 2 is usually conducted in the air. However, it may be conducted in a specific gas atmosphere such as an inert gas atmosphere or in a specific container or system such as a grow box depending on a carrier or a blocking agent to be used, for example.

<Blocking Agent>

The blocking agent is not particularly limited as long as it is a substance having a functional group that is reactive to a tosyl group. However, it is preferably a substance having a hydrophilic functional group capable of preventing non-specific adsorption, for example, of a biological molecule such as a protein, lipid, nucleic acid or cells in a test object, a protein, a luminescent substrate or an light-absorbing substance, or the like in a measurement reagent to the surface of a carrier.

Examples of the functional group that is reactive to a tosyl group include nucleophilic groups such as an amino group and a mercapto group.

Examples of the hydrophilic functional group include a hydroxyl group, a carboxyl group, a sulfonic acid group, a phosphoric acid group, a sugar-containing group, a zwitter ion-containing group, and a polyethyleneglycol-containing group.

The blocking agent is preferably water-soluble from the viewpoint that, for example, non-specific adsorption to a probe-bound carrier can be more inhibited. The term "water-soluble" used herein refers to a feature of being mixed with water at an arbitrary ratio or being dissolved in an amount of not less than 10 mg in 1 g of water at 25° C.

The blocking agent may be any of a low-molecular-weight compound, a biological polymer such as a peptide or a protein, and a synthetic polymer. However, a biological polymer or a synthetic polymer is preferable because it is highly effective for inhibiting non-specific adsorption due to steric hindrance. A synthetic polymer is more preferable in that a biologically derived substance is not brought into a measurement system.

Examples of a low-molecular-weight compound that functions as a blocking agent include tris(hydroxymethyl)aminomethane and ethanolamine. Tris(hydroxymethyl)aminomethane is preferable in that non-specific adsorption can be particularly inhibited.

Examples of a biological polymer that functions as a blocking agent include bovine serum albumin (BSA), casein, and gelatin. BSA is preferable in that non-specific adsorption can be particularly inhibited, for example.

Examples of a publicly known synthetic polymer that functions as a blocking agent include a copolymer of vinyl monomers having a hydrophilic polymer such as polyoxyethylene as a side chain, a block copolymer of a hydrophilic polymer such as polyoxyethylene and a different polymer, and a hydrophilic polymer such as polyoxyethylene having a functional group on one end thereof. In particular, a synthetic polymer having a structure in which one end of polyoxyethylene has a polyamine disclosed in JP 2008-170417 A is preferably used in the present invention because it has an effect of improving reactivity by aligning the orientation of a probe such as an antibody, in addition to an effect of inhibiting non-specific adsorption to the surface of a carrier. Examples of such blocking agent include Blockmaster CE510 or CE210 manufactured by JSR Life Sciences Corporation.

In the case of using the above-described blocking agent, it is preferable to use the blocking agent in an amount at which a proportion of area S2 that is occupied by one tosyl group on the surface of a carrier obtained in step 2 with respect to area S1B that is occupied by one tosyl group on the surface of a carrier obtained in step 1 (S2/S1B×100%) falls within the range described below from the viewpoint that, for example, high sensitivity can be achieved upon diagnosis, detection, or the like with the use of the obtained carrier.

In one aspect in which a magnetic particle is used as a carrier, the amount of the blocking agent used in step 2 is preferably not less than 1 part by mass and more preferably not less than 2 parts by mass with respect to 100 parts by mass of magnetic particles from the viewpoint that, for example, high sensitivity can be achieved upon diagnosis, detection, or the like with the use of the obtained probe-bound carrier. In addition, the upper limit thereof is preferably not more than 200 parts by mass and more preferably not more than 100 parts by mass.

Area Occupied by One Tosyl Group on the Surface of Probe-Bound Carrier

The area that is occupied by one tosyl group on the surface of a probe-bound carrier (each of area S2 that is occupied by one tosyl group on the surface of a carrier obtained in step 2 and area S2' that is occupied by one tosyl group on the surface of a probe-bound carrier) is preferably not less than 15 Å$^2$/tosyl group.

As a result of intensive studies, the present inventors found that a probe-bound carrier having such an area is unlikely to cause non-specific adsorption and has high probe activity.

In addition, each of area S2 and area S2' is preferably not less than 30 Å$^2$/tosyl group, more preferably not less than 40 Å$^2$/tosyl group, and particularly preferably not less than 45 Å$^2$/tosyl group from the viewpoint that, for example, non-specific adsorption is reduced and probe activity is improved.

Remaining tosyl groups tend to cause non-specific adsorption of a biologically relevant substance. The use of a carrier having remaining tosyl groups upon diagnosis, detection, or the like tends to cause an increase in noise. Therefore, tosyl groups may not be present on the surface of a probe-bound carrier.

The proportion of area S2 that is occupied by one tosyl group on the surface of a carrier obtained in step 2 with respect to area S1A that is occupied by one tosyl group on the surface of a carrier used in step 1 (S2/S1A×100%) and the proportion of area S2' area that is occupied by one tosyl group on the surface of a probe-bound carrier with respect to area S1A' that is occupied by one tosyl group on the surface of a carrier to which a probe is not yet bound (S2'/S1A'×100%) are each preferably not less than 140%, more preferably from 150% to 250%, further preferably from 160% to 220%, and particularly preferably from 170% to 190%.

Tosyl groups are reduced in a probe-bound carrier having the area proportion that falls within the above range such that non-specific adsorption of a biologically relevant substance such as a protein or a nucleic acid can be sufficiently inhibited. The use of the carrier allows achieving a low level of noise and a high S/N ratio upon diagnosis, detection or the like and especially immunoassay such as CLIA or CLEIA.

In a case in which the area proportion is below the lower limit of the above range, non-specific adsorption of a biologically relevant substance tends to be promoted. In a case in which the area proportion exceeds the upper limit of the above range, a probe-bound carrier to which a sufficient amount of probes are bound tends not to be obtained. In such a case, high signals might not be obtained upon diagnosis, detection, or the like with the use of the carrier.

The proportion of area S2 that is occupied by one tosyl group on the surface of a carrier obtained in step 2 with respect to area S1B that is occupied by one tosyl group on the surface of a carrier obtained in step 1 (S2/S1B×100%) is preferably not less than 110%, more preferably from 115% to 160%, further preferably from 120% to 150%, and particularly preferably from 125% to 140%.

Tosyl groups are reduced in a probe-bound carrier having the area proportion that falls within the above range such that non-specific adsorption of a biologically relevant substance such as a protein or a nucleic acid can be sufficiently inhibited. The use of the carrier allows achieving a low level of noise and a high S/N ratio upon diagnosis, detection or the like and especially immunoassay such as CLIA or CLEIA.

In a case in which the area proportion is below the lower limit of the above range, non-specific adsorption of a biologically relevant substance tends to be promoted. In a case in which the area proportion exceeds the upper limit of the above range, a probe-bound carrier to which a sufficient amount of probes are bound tends not to be obtained. In such a case, high signals might not be obtained upon diagnosis, detection, or the like with the use of the carrier.

<Intended Use>

A probe-bound carrier obtained in the present method and a probe-bound carrier in one embodiment of the present invention can be preferably used for diagnosis or detection of a target substance and especially for immunoassay such as CLIA or CLEIA. Thus, they can be preferably used for an in-vitro diagnostic agent or for detection of a biologically relevant substance. Therefore, the probe-bound carrier can also be regarded as an in-vitro diagnostic agent or a biologically relevant substance detection agent containing the probe-bound carrier. Specifically, the probe-bound carrier can be used as an affinity carrier such as a compound carrier particle in the field of biochemistry and a chemical binding carrier particle used for a diagnostic agent. The probe-bound carrier is preferably used for immunodiagnosis or nucleic acid detection and particularly preferably used as a probe-bound particle for immunoassay, to which a probe such as an antigen or an antibody is bound.

The above-described target substance is not particularly limited. However, it is preferably a substance that specifically binds to the probe. Specific examples thereof include an immunoassay reagent and a biologically relevant substance or a chemical substance contained in an inspection sample or the like.

The biologically relevant substance is any biologically relevant substance. Examples thereof include an in-vivo substance, a substance induced from an in-vivo substance, and a substance that can be used in vivo. The biologically relevant substance is not particularly limited. However, examples thereof include proteins (e.g., enzymes, antibodies, aptamers, and receptors), peptides (e.g., glutathione), nucleic acids (e.g., DNA and RNA), sugars, lipids, and other cells or substances (e.g., blood-derived substances including various blood cells such as platelets, erythrocytes, and leukocytes and various floating cells).

<Method of Detecting or Separating Target Substance>

The probe-bound carrier is used in a method of detecting or separating a target substance in one embodiment of the present invention (hereinafter also referred to as "the present detection method").

In the present detection method, as the probe-bound carrier is used, it is possible to detect a target substance for detection with remarkably high sensitivity.

In one example of the detection method, the probe-bound carrier is brought into contact with a target substance in a test object, thereby allowing the target substance to be trapped via a probe contained in the probe-bound carrier on the carrier and then to react with a secondary probe. At such time, it is possible to detect the target substance by a fluorescence or enzyme reaction with the use of a phosphor, an isotope, or a probe labeled with an enzyme or the like as a secondary probe, and if necessary, a luminescent reagent or the like.

One example of such a separation method is a method in which the probe-bound carrier is allowed to react with a target substance, and then, the carrier and the substance are magnetically collected and washed, thereby separating and removing components other than the target substance.

EXAMPLES

Hereinafter, the present invention is described in detail with reference to the Examples. However, the present invention is not limited to these Examples.

[Particle Size Measurement]

The particle size of each magnetic particle was measured by Multisizer4e (manufactured by Beckman Coulter Inc.). To 100 mL of an electrolyte solution (ISOTON II manufactured by Beckman Coulter Inc.), 1% by mass magnetic particles dispersed in a 0.1% by mass Tween 20 aqueous solution were added until the value indicated by a concentration sensor reached a level of from 4% to 10%. The particle sizes of 50,000 particles were measured and the average value thereof was calculated, thereby determining the volume average particle size.

[Quantitative Determination of Tosyl Groups]

Magnetic particles in an amount of 100 mg (magnetic particles obtained in Synthesis Example 1 or magnetic particles after each step) dispersed in 1 mL of water were collected in a microtube, and 100 μL of ethylenediamine was added, thereby allowing a reaction to proceed at 40° C. for 15 hours. After the reaction, the microtube was placed on a magnetic stand, thereby recovering the supernatant. The supernatant in an amount of 20 μL was analyzed by ion chromatography (system: ICS2000 manufactured by DIONEX Corporation; column: AS18; detection: electric conductivity; flow rate: 1.0 mL/minute; measurement time: 30 minutes; eluent: 50 mM potassium hydroxide aqueous solution), and the area of a peak that appeared at the retention time point of around 23 minutes was determined. Separately, the amount of surface tosyl groups per 100 mg of magnetic particles was calculated based on a calibration curve obtained by analyzing sodium p-toluenesulfonate by ion chromatography.

[Calculation of Area Occupied by One Tosyl Group on Surface of Magnetic Particle]

The area occupied by one tosyl group on the surface of a magnetic particle is determined by the following formula.

Area occupied by one tosyl group on the surface of a magnetic particle=a surface area of a magnetic particle/the number of surface tosyl groups Specifically, the area was calculated by the following formula.

Area occupied by one tosyl group on the surface of a magnetic particle [Å$^2$/tosyl group]=1/(1.004× specific gravity of magnetic particle [g/cm$^3$]× particle size [μm]×the amount of tosyl groups [mmol/g])

Specific gravity of the magnetic particle used in the Examples was obtained in the following manner.

A powder of magnetic particles in an amount of 30 mg was placed in a simultaneous thermogravimetric analyzer (STA7300 manufactured by Hitachi High-Tech Science Corporation), followed by measurement under the following conditions: temperature increase rate: 10° C./minute; limit temperature: 500° C.; hold time: 20 minutes; sampling time: 1.0 second; gas species: nitrogen; gas flow rate: 200 mL/minute. Thus, the percent by mass (% by mass) of iron oxide and that of a resin contained in magnetic particles were each obtained. The specific gravity of the magnetic particle was calculated based on each percent by mass (% by mass) obtained above at a specific gravity of iron oxide of 5.2 [g/cm$^3$] and a specific gravity of the resin of 1.1 [g/cm$^3$].

[Quantitative Determination of Amount of Binding Antibodies]

Antibodies bound to magnetic particles were quantitatively determined using a BCA Protein Assay Kit (manufactured by Thermo Fisher Scientific Inc.).

At first, each of 50 μL of MES buffer solutions (0.1 mol/L), in which 0 μg, 5 μg, 10 μg, or 15 μg of antibodies were dissolved, was dispensed into a microtube, and 1 mL of a working reagent prepared by mixing a reagent A and a reagent B included in the kit at 50/1 (v/v) was added to each microtube. After incubation at 37° C. for 30 minutes, each microtube was placed on a magnetic stand, thereby recovering the supernatant. Thereafter, OD 562 was measured and thereby creating a calibration curve.

Subsequently, 1 mg of anti-PSA antibody-bound magnetic particles dispersed in 50 μL of an MES buffer solution (0.1 mol/L) were collected in each microtube. The working reagent was added in an amount of 1 mL thereto. After incubation at 37° C. for 30 minutes, each microtube was placed on a magnetic stand, thereby recovering the supernatant. Thereafter, OD 562 was measured. The amount of binding antibodies was calculated based on a calibration curve.

[Chemiluminescence Enzyme Immunoassay (CLEIA)]

To each of wells 1 and 2 of a white 96-well plate, 15 μg of anti-PSA antibody-bound magnetic particles, which were dispersed in 50 μL of a TBS-T buffer solution (137 mmol/L sodium chloride, 2.7 mmol/L potassium chloride, 25 mmol/L tris(hydroxymethyl)aminomethane hydrochloride (hereinafter also referred to as "Tris-HCl"), 0.1% by mass Tween 20, pH 7.4), were added.

Next, for noise measurement, 10 μL of a BSA/TBS buffer solution (1% by mass BSA, 137 mmol/L sodium chloride, 2.7 mmol/L potassium chloride, 25 mmol/L Tris-HCl, pH 7.4) was added to well 1, and for signal measurement, 10 μg of an PSA antigen which was dissolved in 10 μL of a BSA/TBS buffer solution (containing 1% by mass BSA) was added to well 2, thereby allowing a reaction to proceed at 37° C. for 10 minutes. Then, antibody-bound particles were magnetically collected, the supernatant was removed, and the particles were washed with a TBS-T buffer solution. This operation of magnetically collecting and washing magnetic particles was repeated five times in total. Thereafter, 50 μL of anti-PSA antibodies labelled with alkaline phosphatase were added, thereby allowing a reaction to proceed at 37° C. for 10 minutes. After the reaction, an operation of magnetically collecting and washing magnetic particles was conducted five times using a TBS-T buffer solution in the manner described above, and 50 μL of a luminescent substrate (a Class III series LUMIPULSE substrate solution manufactured by FUJIREBIO Inc.) was added. Luminescence intensities of noises and signals were measured using a luminometer 5 minutes after the addition of a luminescent substrate.

Synthesis Example 1

Acetone was added to an oily magnetic fluid ("EXP series EMG" manufactured by Ferrotec Holdings Corporation), thereby allowing particles to be precipitated and deposited. The particles were dried. Thus, surface-hydrophobized ferrite (iron oxide) magnetic body particles (average primary particle size: 0.01 μm) were obtained.

Next, 30 g of polystyrene particles (volume average particle size: 1.5 μm) and 15 g of the hydrophobized magnetic body particles were sufficiently mixed by a mixer, and the mixture was treated using an NHS-0 type hybridization system (manufactured by Nara Machinery Co., Ltd.) at a circumferential velocity of a blade (stirring blade) of 100 m/second (16,200 rpm) for 5 minutes. Thus, base particles (particle size: 2.0 μm) having a magnetic body layer consisting of magnetic body particles on its surface were obtained.

Subsequently, 375 g of an aqueous solution containing sodium dodecyl sulfate at a concentration of 0.50% by mass was introduced into a 1 L separable flask. Then, 15 g of the base particles having a magnetic body layer were added and dispersed by a homogenizer, 6 followed by heating to 60° C.

A pre-emulsion prepared by adding 27 g of methyl methacrylate (hereinafter referred to as "MMA"), 3 g of trimethylol propane trimethacrylate (hereinafter referred to as "TMP"), and 0.6 g of di(3,5,5-trimethylhexanoyl)peroxide (PEROYL 355 manufactured by NOF Corporation (hereinafter referred to as "PEROYL 355")) to 150 g of an aqueous solution containing sodium dodecyl sulfate at a concentration of 0.50% by mass and dispersing the mixture was added dropwise to the 1 L separable flask controlled at 60° C. over 2 hours. After the dropwise addition, the temperature was maintained at 60° C., followed by stirring for 1 hour. Then, a pre-emulsion prepared by adding 13.5 g of glycidyl methacrylate (hereinafter referred to as "GMA"), 1.5 g of TMP, and 0.3 g of PEROYL 355 to 75 g of an aqueous solution containing sodium dodecyl sulfate at a concentration of 0.50% by mass and dispersing the mixture was added dropwise to the 1 L separable flask controlled at 60° C. over 1 hour and 30 minutes. Thereafter, the temperature was increased to 75° C. and polymerization was further allowed to proceed for 2 hours, thereby completing the reaction.

Subsequently, 60 mL of 1 mol/L sulfuric acid was added to the 1 L separable flask and stirred at 60° C. for 6 hours. Then, particles in the separable flask were magnetically separated and washed repeatedly using distilled water. Accordingly, magnetic particles (A) comprising hydroxyl groups were obtained.

Next, magnetic particles (A) were lyophilized, and 1.0 g of the lyophilized magnetic particles (A) were dispersed in 8 mL of pyridine. Then, 0.2 g of p-toluenesulfonyl chloride was added, and the resulting mixture was stirred at room temperature for 2 hours. After the reaction, particles were magnetically separated and washed with acetone 4 times and then with distilled water 4 times, thereby obtaining magnetic particles comprising tosyl groups (B). The particle size was 3.0 μm.

Example 1

The magnetic particles (B) obtained in Synthesis Example 1 in an amount of 10 mg were dispersed in 1.5 mL of a boric acid buffer solution (ammonium sulfate: 0.5 mol/L; boric acid: 0.1 mol/L; pH 9.5) in which ammonium sulfate was dissolved. An antibody against a prostate-specific antigen (PSA) (hereinafter referred to as "anti-PSA antibody") was added in an amount of 100 μg to the magnetic-particle dispersion liquid, thereby allowing a reaction to proceed at 37° C. for 8 hours. Then, 50 μL of CE510 (2.0% by mass, manufactured by JSR Corporation) was added as a blocking agent, thereby allowing a reaction to proceed at 37° C. for 15 hours. After the reaction, the particles were magnetically separated using a magnetic stand and washed with a washing liquid (25 mmol/L Tris-HCl containing 0.01% by mass Tween 20, pH 7.4) repeatedly, thereby obtaining anti-PSA antibody-bound magnetic particles (C-1).

Example 2

Anti-PSA antibody-bound magnetic particles (C-2) were obtained by conducting the same operation as in Example 1 except that the blocking reaction time was set to 6 hours.

Example 3

Anti-PSA antibody-bound magnetic particles (C-3) were obtained by conducting the same operation as in Example 1 except that BSA was used as a blocking agent.

Example 4

The magnetic particles (B) obtained in Synthesis Example 1 were dispersed in an amount of 10 mg in 1.0 mL of a boric acid buffer solution (0.1 mol/L, pH9.5), and 100 μg of an anti-PSA antibody was added. Subsequently, 0.5 mL of a boric acid buffer solution (ammonium sulfate: 1.5 mol/L; boric acid: 0.1 mol/L; pH 9.5), in which ammonium sulfate was dissolved, was added, thereby allowing a reaction to proceed at 37° C. for 8 hours. Then, 50 μL of CE510 (2.0% by mass, manufactured by JSR Corporation) was added as a blocking agent, thereby allowing a reaction to proceed at 37° C. for 15 hours. After the reaction, the particles were magnetically separated using a magnetic stand, washed with a washing liquid (25 mmol/L Tris-HCl containing 0.01% by mass Tween 20, pH 7.4) repeatedly, and diluted with the washing liquid such that the particle concentration was adjusted to 0.03% by mass. Thus, anti-PSA antibody-bound magnetic particles (C-4) were obtained.

Example 5

Anti-PSA antibody-bound magnetic particles (C-5) were obtained by conducting the same operation as in Example 1 except that the ammonium sulfate concentration of the boric acid buffer solution in which ammonium sulfate was dissolved was set to 1.0 mol/L.

Example 6

Anti-PSA antibody-bound magnetic particles (C-6) were obtained by conducting the same operation as in Example 2 except that Dynabeads M-280 Tosylactivated (manufactured by Thermo Fisher Scientific Inc.) were used as particles.

Example 7

Anti-PSA antibody-bound magnetic particles (C-7) were obtained by conducting the same operation as in Example 1 except that the ammonium sulfate concentration of the boric acid buffer solution in which ammonium sulfate was dissolved was set to 3.0 mol/L.

Comparative Example 1

Anti-PSA antibody-bound magnetic particles (D-1) were obtained by conducting the same operation as in Example 1 except that magnetic particles (A) were used as magnetic particles, instead of magnetic particles (B).

Comparative Example 2

Anti-PSA antibody-bound magnetic particles (D-2) were obtained by conducting the same operation as in Example 1 except that blocking was not conducted.

Comparative Example 3

Anti-PSA antibody-bound magnetic particles (D-3) were obtained by conducting the same operation as in Example 1 except that the blocking reaction time was set to 1 hour.

Comparative Example 4

Anti-PSA antibody-bound magnetic particles (D-4) were obtained by conducting the same operation as in Example 6 except that blocking was not conducted.

Comparative Example 5

Anti-PSA antibody-bound magnetic particles (D-5) were obtained by conducting the same operation as in Example 6 except that the blocking reaction time was set to 1 hour.

What is claimed is:

1. A method of producing a probe-bound carrier, which comprises:
    step 1a of mixing a carrier having tosyl groups with ammonium sulfate to form a first mixture, wherein ammonium sulfate concentration of the first mixture is from 0.2 to 1.0 mol/L;
    step 1b mixing a probe with the first mixture to form a second mixture; and
    step 2 of reducing the amount of tosyl groups on a surface of the carrier to reduce the density of the tosyl groups on the surface of the carrier by mixing the second mixture with a blocking agent,
    wherein a proportion of area S2 that is occupied by one tosyl group on the surface of the carrier obtained in the step 2 relative to area S1A that is occupied by one tosyl group on the surface of the carrier in the step 1, which is expressed as S2/S1A×100%, is not less than 140%.

2. The production method according to claim 1, wherein a proportion of area S2 that is occupied by one tosyl group on a surface of the carrier obtained in the step 2 with respect to area S1B that is occupied by one tosyl group on a surface of the carrier obtained in the step 1, which is expressed as S2/S1B×100%, is not less than 110%.

3. The production method according to claim 1, wherein the carrier is a magnetic particle.

4. The production method according to claim 3, wherein the magnetic particle has a core-shell structure.

5. The production method according to claim 3, wherein a volume average particle size of the magnetic particle is from 0.1 to 20 μm.

6. The production method according to claim 1, wherein the second mixture is a liquid, and pH of the liquid is from 6 to 12.

7. The production method according to claim 1, wherein the area S1A that is occupied by one tosyl group on a surface of the carrier used in the step 1 is not less than 5 Å$^2$/tosyl group.

TABLE 1

| | Particle | | Step 1 | | | Step 2 | | S2/ S1A | S2/ S1B | Amount of probes bound | CLEIA | | |
|---|---|---|---|---|---|---|---|---|---|---|---|---|---|
| | Type | S1A [Å$^2$] | Ammonium sulfate concentration [mol/L] | S1B [Å$^2$] | Type | Reaction time [hour] | S2 [Å$^2$] | ×100% | ×100% | [μg/mg beads] | Signal | Noise | Signal/ Noise |
| Example 1 | Particle (B) | 32 | 0.5 | 43 | CE510 | 15 | 55 | 172% | 128% | 8 | 1187420 | 165 | 7196 |
| Example 2 | Particle (B) | 32 | 0.5 | 43 | CE510 | 6 | 50 | 156% | 116% | 8 | 1206538 | 196 | 6156 |
| Example 3 | Particle (B) | 32 | 0.5 | 43 | BSA | 15 | 49 | 153% | 114% | 8 | 1194769 | 214 | 5583 |
| Example 4 | Particle (B) | 32 | 0.5 | 43 | CE510 | 15 | 57 | 178% | 133% | 8 | 1145724 | 368 | 3113 |
| Example 5 | Particle (B) | 32 | 1 | 43 | CE510 | 15 | 50 | 156% | 116% | 8 | 1002391 | 312 | 3213 |
| Example 6 | Dynabeads M-280 Tosylactivated | 10 | 0.5 | 12 | CE510 | 6 | 15 | 150% | 125% | 9 | 923932 | 309 | 2990 |
| Example 7 | Particle (B) | 32 | 3 | 44 | CE510 | 15 | 56 | 175% | 127% | 8 | 912547 | 343 | 2660 |
| Comparative Example 1 | Particle (A) | 0 | 0.5 | 0 | CE510 | 15 | 0 | — | — | 0 | 8493 | 160 | 53 |
| Comparative Example 2 | Particle (B) | 32 | 0.5 | 43 | None | — | 43 | 134% | 100% | 8 | 912456 | 1254 | 728 |
| Comparative Example 3 | Particle (B) | 32 | 0.5 | 43 | CE510 | 1 | 44 | 138% | 102% | 8 | 925436 | 1004 | 922 |
| Comparative Example 4 | Dynabeads M-280 Tosylactivated | 10 | 0.5 | 12 | None | — | 12 | 120% | 100% | 8 | 798120 | 1565 | 510 |
| Comparative Example 5 | Dynabeads M-280 Tosylactivated | 10 | 0.5 | 12 | CE510 | 1 | 13 | 130% | 108% | 8 | 767893 | 1398 | 549 |

8. The production method according to claim 1, wherein the probe is a protein or nucleic acid.

9. The production method according to claim 1, wherein a mixing time in the step 1b is not less than 2 hours.

10. The production method according to claim 1, wherein mixing in the step 2 is not less than 2 hours.

11. The production method according to claim 1, wherein the blocking agent is at least one substance selected from the group consisting of, casein, gelatin, a water-soluble low-molecular-weight compound having an amino group and a hydroxyl group, and a synthetic polymer having a polyethyleneglycol-containing group.

12. The production method according to claim 1, wherein the blocking agent is a synthetic polymer having a polyethyleneglycol-containing group.

* * * * *